(12) United States Patent
Sweeney (10) Patent No.: US 9,980,820 B2
(45) Date of Patent: May 29, 2018

(54) VERTEBRAL PROSTHESIS AND SPINAL FIXATION SYSTEM

(75) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 1062 days.

(21) Appl. No.: 12/906,594

(22) Filed: Oct. 18, 2010

(65) Prior Publication Data

US 2011/0035009 A1 Feb. 10, 2011

Related U.S. Application Data

(63) Continuation of application No. 10/956,455, filed on Oct. 1, 2004, now Pat. No. 7,883,543.

(51) Int. Cl.
| | |
|---|---|
| *A61F 2/44* | (2006.01) |
| *A61B 17/70* | (2006.01) |
| *A61F 2/28* | (2006.01) |
| *A61F 2/30* | (2006.01) |

(52) U.S. Cl.
CPC ............ *A61F 2/44* (2013.01); *A61B 17/7059* (2013.01); *A61F 2002/2835* (2013.01); *A61F 2002/3052* (2013.01); *A61F 2002/3055* (2013.01); *A61F 2002/30405* (2013.01); *A61F 2002/30495* (2013.01); *A61F 2002/30507* (2013.01); *A61F 2002/30517* (2013.01); *A61F 2002/30578* (2013.01); *A61F 2002/30601* (2013.01); *A61F 2002/30777* (2013.01); *A61F 2002/30785* (2013.01); *A61F 2220/0025* (2013.01); *A61F 2310/00023* (2013.01); *A61F 2310/00179* (2013.01)

(58) Field of Classification Search
USPC ....... 623/17.11–17.16; 606/246, 280, 70, 71, 606/281, 282
See application file for complete search history.

(56) References Cited

U.S. PATENT DOCUMENTS

| | | | |
|---|---|---|---|
| 4,401,112 A | 8/1983 | Rezaian | |
| 4,553,273 A | 11/1985 | Wu | |
| 4,636,217 A | 1/1987 | Ogilvie et al. | |
| 4,657,550 A * | 4/1987 | Daher | 623/17.11 |
| 4,932,975 A | 6/1990 | Main et al. | |
| 5,147,404 A | 9/1992 | Downey | |
| 5,236,460 A | 8/1993 | Barber | |
| 5,246,458 A * | 9/1993 | Graham | 623/17.14 |
| 5,261,911 A | 11/1993 | Carl | |
| 5,324,290 A | 6/1994 | Zdeblick et al. | |
| 5,425,772 A | 6/1995 | Brantigan | |
| 5,458,638 A | 10/1995 | Kuslich et al. | |
| 5,458,641 A | 10/1995 | Ramirez Jimenez | |
| 5,522,899 A | 6/1996 | Michelson | |

(Continued)

OTHER PUBLICATIONS

International Search Report and Written Opinion for Application No. PCT/US05/34979, dated Oct. 20, 2006, 6 pages.

*Primary Examiner* — Anu Ramana (74) *Attorney, Agent, or Firm* — Foley & Lardner LLP (57) ABSTRACT

A vertebral prosthesis and spinal fixation system includes a vertebral prosthesis having a height adjustable shaft and an anchoring mechanism coupled to the shaft. The system further includes a spinal fixation device and a number of bone screws. The bone screws attach the fixation device to the vertebral prosthesis via the anchoring mechanism.

8 Claims, 9 Drawing Sheets

(56) References Cited

U.S. PATENT DOCUMENTS

| | | |
|---|---|---|
| 5,601,553 A | 2/1997 | Trebing et al. |
| 5,603,713 A | 2/1997 | Aust et al. |
| 5,665,122 A | 9/1997 | Kambin |
| 5,702,453 A | 12/1997 | Rabbe et al. |
| 5,776,197 A | 7/1998 | Rabbe et al. |
| 5,776,198 A | 7/1998 | Rabbe et al. |
| 5,776,199 A | 7/1998 | Michelson |
| 5,895,427 A | 4/1999 | Kuslich et al. |
| 5,916,267 A | 6/1999 | Tienboon |
| 6,015,436 A | 1/2000 | Schonhoffer |
| 6,045,552 A | 4/2000 | Zucherman et al. |
| 6,045,579 A | 4/2000 | Hochshuler et al. |
| 6,080,193 A | 6/2000 | Hochshuler et al. |
| 6,086,613 A | 7/2000 | Camino et al. |
| 6,106,557 A | 8/2000 | Robioneck et al. |
| 6,126,689 A | 10/2000 | Brett |
| 6,149,686 A | 11/2000 | Kuslich et al. |
| 6,159,211 A | 12/2000 | Boriani et al. |
| 6,159,244 A | 12/2000 | Suddaby |
| 6,174,334 B1 | 1/2001 | Suddaby |
| 6,183,517 B1 | 2/2001 | Suddaby |
| 6,296,665 B1 | 10/2001 | Strnad et al. |
| 6,344,057 B1 | 2/2002 | Rabbe et al. |
| 6,375,682 B1 | 4/2002 | Fleishmann et al. |
| 6,395,030 B1 | 5/2002 | Songer et al. |
| 6,409,766 B1 | 6/2002 | Brett |
| 6,413,278 B1 | 7/2002 | Marchosky |
| 6,419,705 B1 * | 7/2002 | Erickson .................... 623/17.16 |
| 6,432,106 B1 | 8/2002 | Fraser |
| 6,443,987 B1 | 9/2002 | Bryan |
| 6,447,544 B1 | 9/2002 | Michelson |
| 6,488,710 B2 | 12/2002 | Besselink |
| 6,500,206 B1 | 12/2002 | Bryan |
| 6,520,993 B2 | 2/2003 | James et al. |
| 6,558,423 B1 | 5/2003 | Michelson |
| 6,562,073 B2 | 5/2003 | Foley |
| 6,565,571 B1 | 5/2003 | Jackowski et al. |
| 6,576,017 B2 | 6/2003 | Foley et al. |
| 6,613,051 B1 | 9/2003 | Luk et al. |
| 6,682,561 B2 | 1/2004 | Songer et al. |
| 6,692,495 B1 | 2/2004 | Zacouto |
| 6,740,088 B1 | 5/2004 | Kozak et al. |
| 7,048,766 B2 * | 5/2006 | Ferree ........................ 623/17.16 |
| 7,850,735 B2 * | 12/2010 | Eisermann et al. ....... 623/17.14 |
| 2002/0055782 A1 | 5/2002 | Bagby |
| 2003/0065396 A1 | 4/2003 | Michelson |
| 2003/0139813 A1 | 7/2003 | Messerli et al. |
| 2003/0171813 A1 | 9/2003 | Kiester |
| 2004/0172129 A1 | 9/2004 | Schafer et al. |
| 2005/0060034 A1 | 3/2005 | Berry et al. |
| 2005/0071007 A1 | 3/2005 | Malek |
| 2005/0085910 A1 | 4/2005 | Sweeney |
| 2005/0165487 A1 * | 7/2005 | Muhanna et al. ......... 623/17.15 |
| 2005/0228501 A1 | 10/2005 | Miller et al. |
| 2005/0251261 A1 | 11/2005 | Peterman |
| 2006/0100710 A1 | 5/2006 | Gutlin et al. |

* cited by examiner

VERTEBRAL PROSTHESIS AND SPINAL FIXATION SYSTEM

CROSS-REFERENCE TO RELATED APPLICATION

This application is a continuation of application Ser. No. 10/956,455, filed Oct. 1, 2004, which is incorporated herein by reference in its entirety.

FIELD OF THE INVENTION

The present invention relates to a vertebral prosthesis and related spinal fixation system. In particular, the present invention relates to a vertebral prosthesis that is designed to be used in conjunction with a spinal fixation plate.

BACKGROUND OF THE INVENTION

The spinal column is comprised of twenty-six interlocking vertebrae. These vertebrae are separated by disks. The spine provides load-bearing support for one-half of the body's mass and it protects the nerves of the spinal column. The disks provide shock absorption and facilitate the bending of the spine.

The combination of the vertebrae and disks at each vertebral segment allows for motion of the spine, in particular, flexing, rotation and extension. The motion and support functions of the spine, in combination with the many interlocking parts and nerve roots associated with the spinal column, can result in back pain due to various reasons. Such back pain may result from the degeneration of disks due to age, disease, or injury. Further, vertebral bodies may be compromised due to disease or defects, such as a tumor, or injury, such as fracture.

In certain cases, it may be necessary to remove or replace one or more of the vertebral bodies or disks to alleviate pain or regain spinal functionality. Replacement of a vertebral body is typically required due to an unstable burst fracture, severe compression fracture, or tumor decompression.

A vertebral body replacement procedure typically involves the removal of the disks above and below the compromised vertebral body along with all or a portion of the vertebral body. In place of the removed elements, a strut graft and plate are used make the vertebrae above and below the replaced vertebral body grow together and become one bone. Because the intention of a spinal fusion procedure utilized along with vertebral body replacement is to create solid bone in the area that is excised, the spacer that is inserted to restore normal height may be configured to enhance bone in-growth, which may be enhanced by the addition of bone growth material.

In a vertebral body replacement procedure, the vertebral body is partially or entirely replaced by a vertebral prosthesis. Several vertebral prosthesis designs are known in the art. One such vertebral prosthesis design is shown in U.S. application Ser. No. 10/686,998, titled "Vertebral Prosthesis," which is incorporated by reference herein in its entirety.

When a vertebral prosthesis is utilized to replace a vertebral body, a spinal fixation system may be utilized to stabilize the adjacent vertebrae. Such a spinal fixation system may include a plate designed to be attached to the adjacent vertebrae with bone screws to lock the adjacent vertebrae into position relative to one another. The spinal fixation system may be utilized because the vertebral prosthesis is not configured to provide the stability necessary for fusing the prosthesis with the adjacent vertebrae.

The use of a vertebral prosthesis along with a supplemental spinal fixation system presents certain challenges. Depending on the load carried by the vertebral prosthesis, the prosthesis can collapse into the adjacent bone. Further, the bone screws utilized to attach the spinal fixation plate to the adjacent vertebrae may migrate over time, decreasing the effectiveness of the spinal fixation.

It would be advantageous to provide a vertebral body replacement system that includes a vertebral prosthesis and spinal fixation system that are designed to work in conjunction with one another to address one or more of the above identified challenges presented by current systems. It would also be advantageous to provide a vertebral body replacement system that may be utilized without a supplemental spinal fixation system while still providing the spinal fusion functionality.

It would be desirable to provide a system and/or procedure that provides one or more of these or other advantageous features. Other features and advantages will be made apparent from the present specification. The teachings disclosed extend to those embodiments that fall within the scope of the appended claims, regardless of whether they accomplish one or more of the above-identified needs.

SUMMARY OF THE INVENTION

The invention relates to a spinal implant system having a vertebral prosthesis adapted to be placed adjacent a vertebra. The system further includes at least one bone screw and a spinal fixation device coupled to the prosthesis by the bone screw. The bone screw extends through at least a portion of the vertebra.

The invention further relates to a vertebral prosthesis for replacing a compromised vertebra. The prosthesis includes a shaft having an endplate at one end, and an anchor extending from the endplate. The anchor is adapted to extend into an adjacent vertebra and includes an aperture sized to receive a bone screw.

The invention further relates to a spinal fixation system having a vertebral prosthesis with a shaft. The height of the shaft is adjustable after implantation in a patient without adding or removing components to or from the shaft. An anchoring mechanism is coupled to the shaft. The system further includes a spinal fixation device and a bone screw. The bone screw attaches the spinal fixation device to the anchoring mechanism.

The invention further relates to a method of implanting a vertebral prosthesis. The method includes the steps of opening an aperture in a patient to permit access to a first vertebra located adjacent to a second vertebra, removing at least a portion of the first vertebra, and inserting a vertebral prosthesis into the space created by the removal of the portion of the first vertebra. The method further includes the steps of providing a bone screw and a spinal fixation device, coupling the fixation device to the vertebral prosthesis with the bone screw such that the bone screw extends through at least a portion of the second vertebra, and closing the aperture.

The invention further relates to a method of implanting a vertebral prosthesis. The method includes the steps of opening an aperture in a patient to permit access to a first vertebra located adjacent to a second vertebra, removing at least a portion of the first vertebra, providing a vertebral prosthesis having an anchoring mechanism, and creating a cavity in the second vertebra sized to receive the anchoring mechanism. The method further includes the steps of inserting the vertebral prosthesis into the space created by the removal of the portion of the first vertebra, impacting the anchoring mechanism into the cavity, coupling the prosthesis to the second vertebra with a bone screw, and closing the aperture.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DESCRIPTION OF PREFERRED EMBODIMENTS

Figure 1:
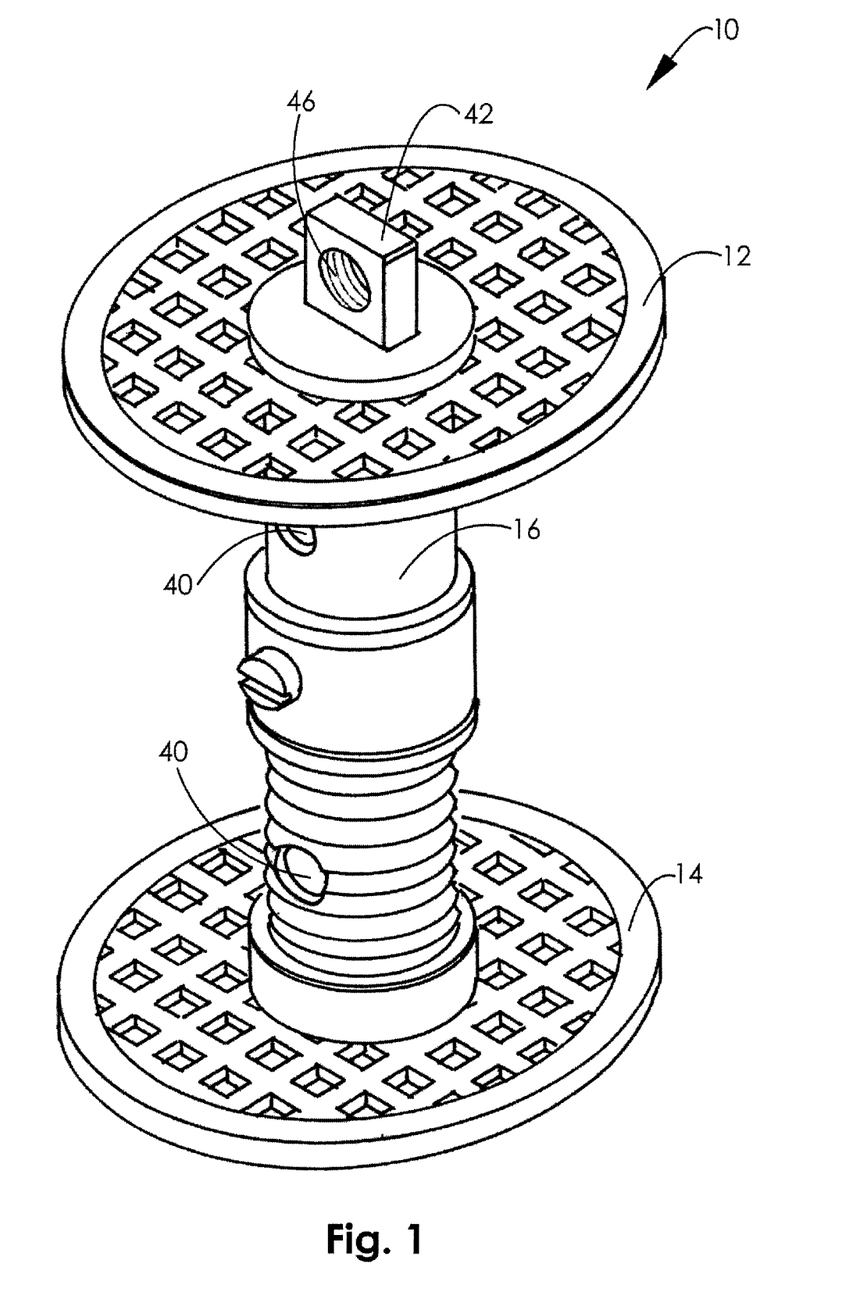
FIG. 1 is a perspective view of a vertebral prosthesis.

Referring to FIG. 1, according to an exemplary embodiment, a vertebral prosthesis 10 includes a pair of endplates, shown as upper endplate 12 and lower endplate 14. The endplates 12, 14 are connected to one another by a shaft 16.

Figure 2:
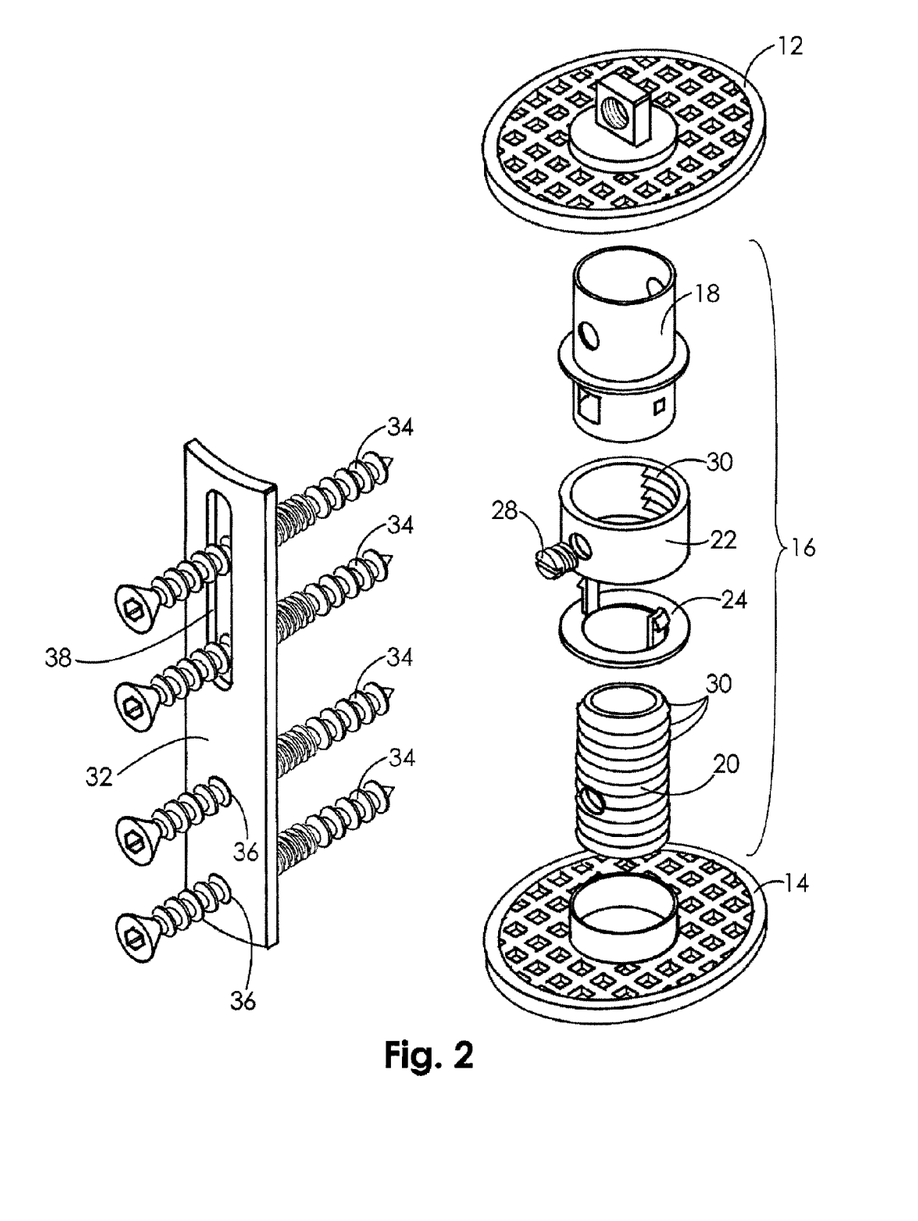
FIG. 2 is an exploded perspective view of a vertebral prosthesis and spinal fixation system.

Referring to FIG. 2, the shaft 16 may include several components, including upper portion 18 and lower portion 20. A locking ring 22 may be held in place by a washer 24 and used to connect lower portion 20 to upper portion 18. In the embodiment shown in FIG. 2, the lower portion 20 is received within cylindrically shaped upper portion 18 and fixed in place by a fixation device, shown a screw 28. The use of the locking ring 22 and screw 28 permits the height of shaft 16 to be adjusted as desired by the surgeon.

Figure 4:
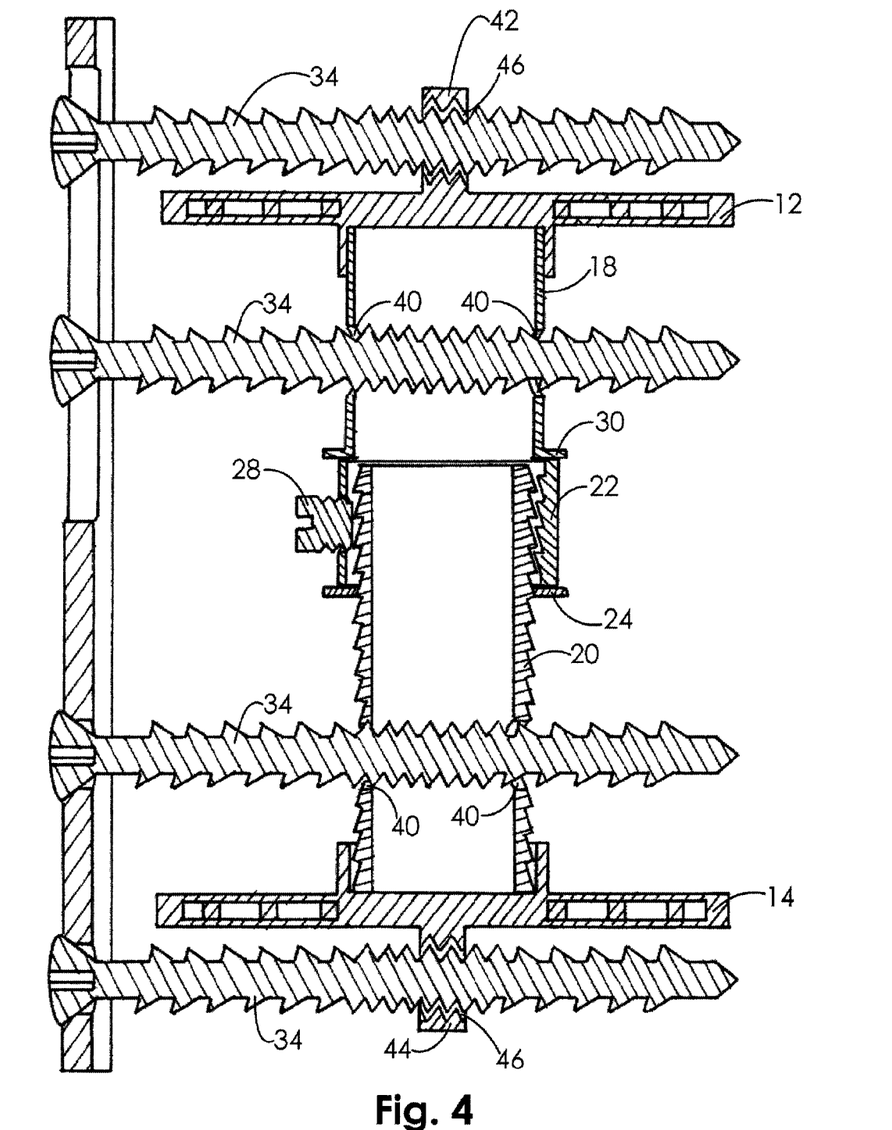
FIG. 4 is a sectional view of a vertebral prosthesis assembled together with a spinal fixation system.
Figure 5:
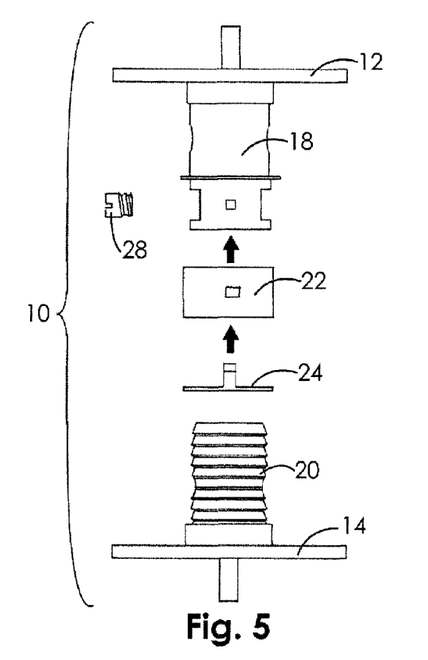
FIG. 5 is an elevation view of the components of a vertebral prosthesis prior to assembly.
Figure 6:
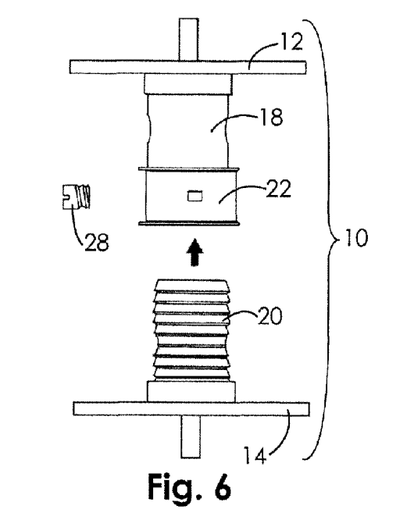
FIG. 6 is an elevation view of the components of a partially assembled vertebral prosthesis.
Figure 7:
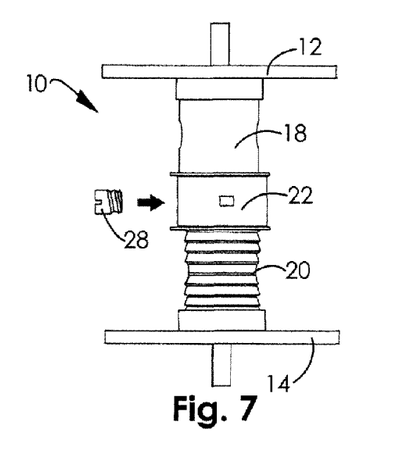
FIG. 7 is an elevation view of the components of a partially assembled vertebral prosthesis.
Figure 8:
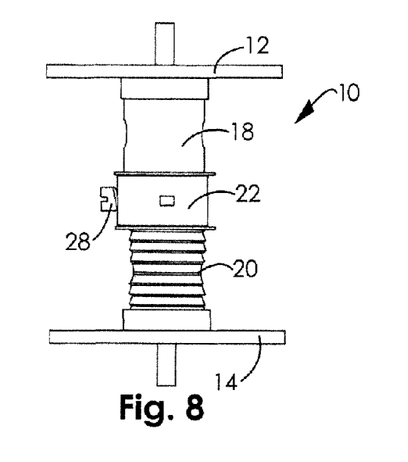
FIG. 8 is an elevation view of an assembled vertebral prosthesis.

Further referring to FIG. 2, in an exemplary embodiment, locking ring 22 locks the upper portion 18 and lower portion 20 into position relative to each other via interlocking teeth 30 on both the locking ring 22 and lower portion 20 that engage one another when screw 28 is tightened, as indicated in FIG. 4.

Further referring to FIG. 2, a spinal fixation system according to an exemplary embodiment is shown as including a spinal fixation device, shown as, but not limited to, locking plate 32, and a number of bone screws 34. The bone screws 34 are configured to extend through a number of apertures in the locking plate 32, shown as holes 36 and slot 38. The spinal fixation device, while shown as locking plate 32 in the embodiment of FIG. 2, may also be a rod or another device suitable to provide for fixation of vertebrae.

Referring to FIGS. 1 and 4, the vertebral prosthesis includes a number of apertures configured to receive and be secured to bone screws 34. In particular, the shaft 16 includes two apertures 40, and the endplates, 12, 14 each have an anchoring mechanism or anchor, shown as, but not limited to, anchors 42, 44, each having a body portion and a threaded aperture 46 configured to receive a bone screw 34. The bone screws 34 are shown as screws, but may also take the form of bolts or other attachment mechanisms in alternative embodiments.

Figure 3:
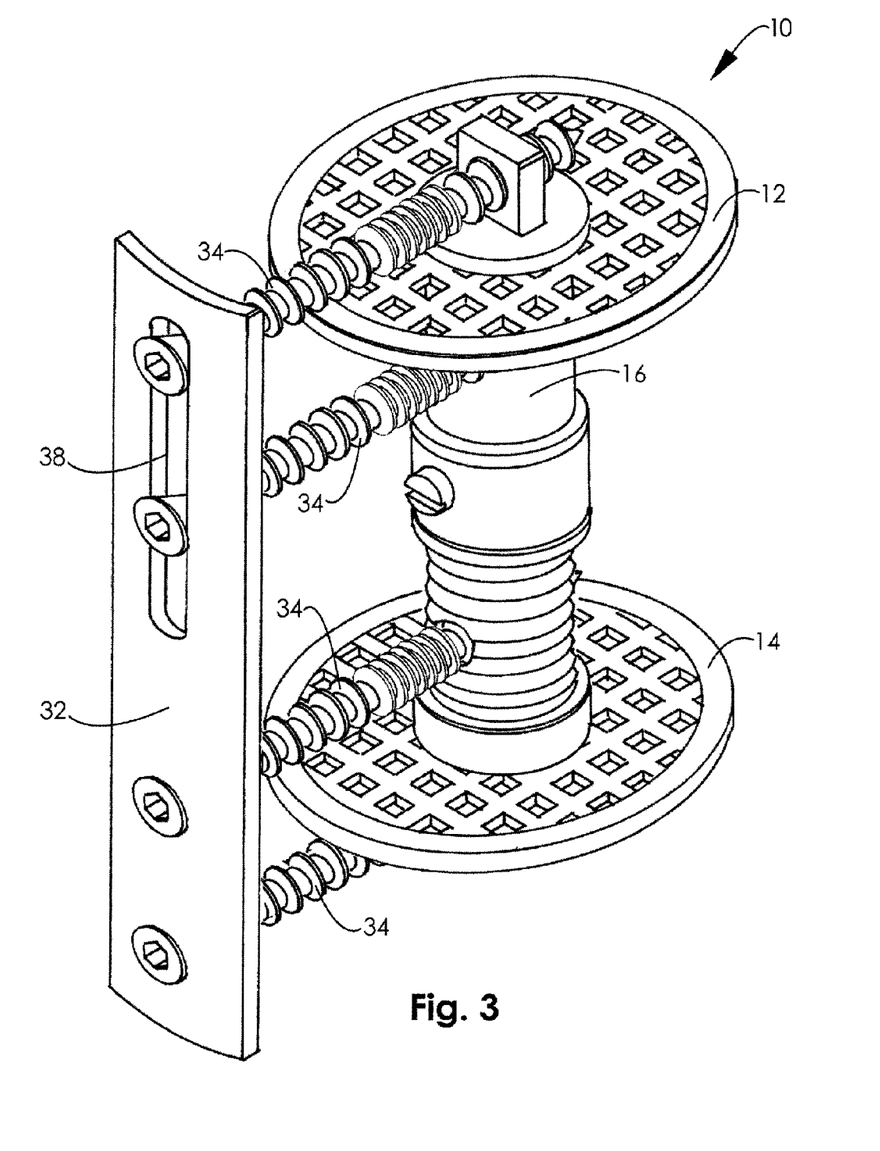
FIG. 3 is a perspective view of a vertebral prosthesis and spinal fixation system.

Referring to FIGS. 3 and 4, the locking plate 32 may be secured to the vertebral prosthesis 10 by screwing the bone screws 34 into the corresponding apertures 40, 46 in the vertebral prosthesis 10. The bone screws 34 and apertures 40, 46 are configured to engage one another such that the bone screws 34 may be adjustably secured to the vertebral prosthesis 10. The bone screws 34 may be self-drilling as is known in the art or may have a cannulated design configured to be used with a drill and driver as described in U.S. application Ser. No. 10/864,673, titled "Spinal Fixation System," which is incorporated herein by reference in its entirety.

In an exemplary embodiment, the endplates are configured to be threaded or screwed on and off of the shaft 16 of the vertebral prosthesis 10 so that endplates 12, 14 may be quickly and easily removed and installed depending on the desired configuration. In other embodiments, the endplates 12, 14 and shaft 16 may be snapped on or twist-locked onto one another. The surgeon may have the choice of several endplates depending on the desired final configuration of the vertebral prosthesis system.

Referring to FIGS. 5-8, the vertebral prosthesis 10 may be assembled by placing the locking ring 22 and washer 24 onto the upper portion 18, followed by inserting the lower portion 20 into the upper portion 18 to the extent necessary to achieve the desired distance between the endplates 12, 14. The screw 28 may then be inserted into the locking ring 22 in order to releasably secure the lower portion 20 relative to the upper portion 18. If necessary, the height may be further adjusted by loosening the screw 28 and changing the position of the lower portion 20 relative to the upper portion 18, followed by retightening of the screw 28.

Figure 9:
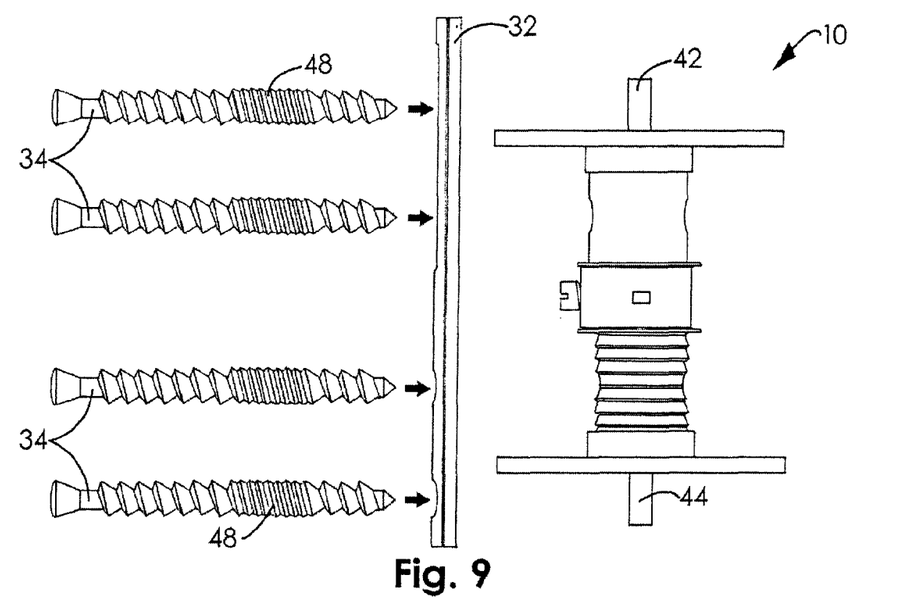
FIG. 9 is an elevation view of a vertebral prosthesis and spinal fixation system prior to assembly with one another.
Figure 10:
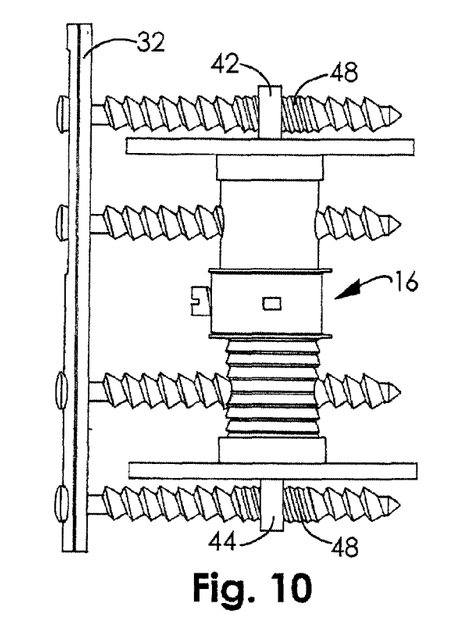
FIG. 10 is an elevation view of a vertebral prosthesis and spinal fixation system after assembly with one another.

FIGS. 9 and 10 illustrate the attachment of the locking plate 32 to the vertebral prosthesis 10. The bone screws 34 are inserted through the apertures in the locking plate 32 and screwed into the corresponding apertures in the vertebral prosthesis 10. Although the use of four bone screws 34 is shown, in other embodiments, a different number of bone screws 34 may be utilized.

Figure 11:
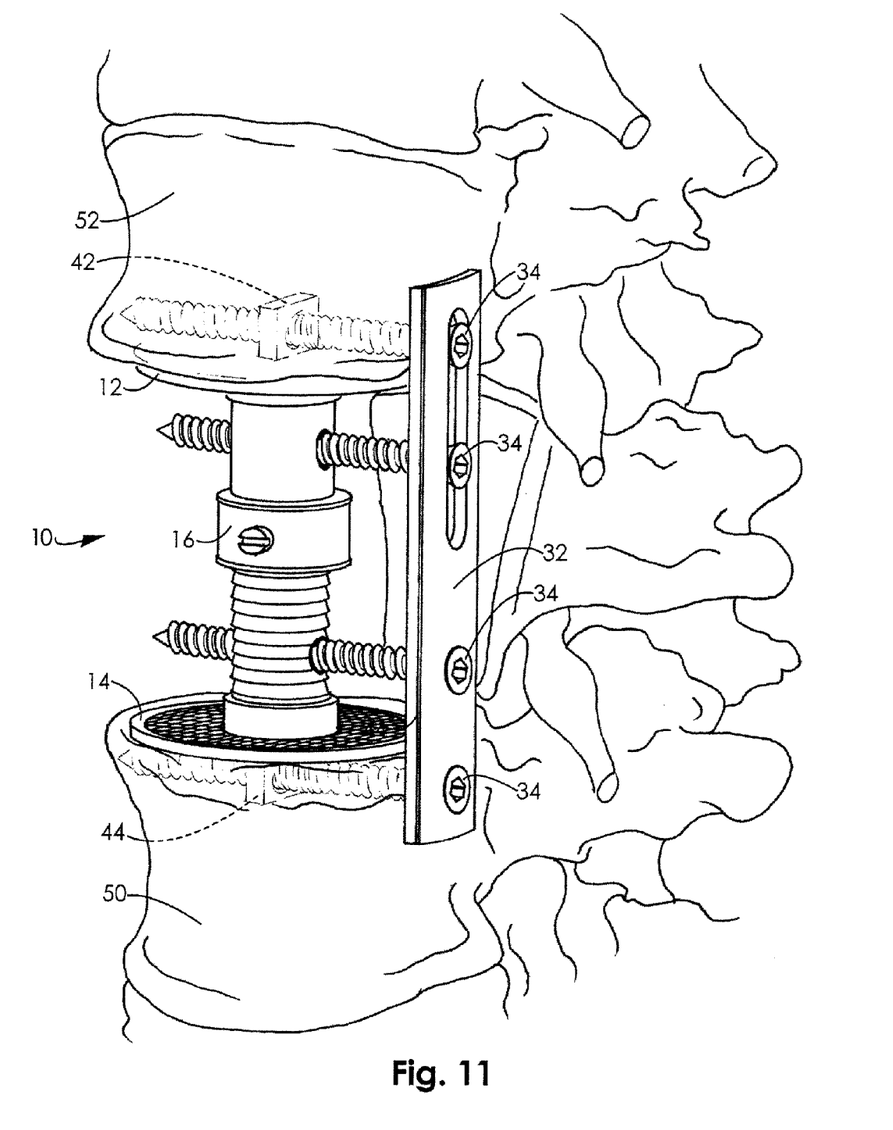
FIG. 11 is a perspective view of a vertebral prosthesis and spinal fixation system inserted into a spine.

Referring to FIGS. 3, 10, and 11, the outer bone screws 34 are configured to engage the anchors 42, 44. To aid in such engagement, a segment 48 of the bone screws 34 may be provided with different threads, such as threads having a different thread pitch, intended to mate with the interior threaded portions of the anchors 42, 44. A similar approach may be utilized with the bone screws 34 that attach to the shaft 16.

FIG. 11 depicts vertebral prosthesis 10 installed in a spine in accordance with one exemplary embodiment. In the example shown, a diseased or injured vertebra has been removed and the vertebral prosthesis 10 has been inserted between a superior vertebra 52 and an inferior vertebra 50. Further, the two natural disks adjacent the removed vertebra have been excised to permit the inferior and superior vertebrae 50, 52 to be fused together as one structure with the vertebral prosthesis 10.

Attachment of the locking plate 32 to the vertebral prosthesis 10 is intended to create a unified vertebral prosthesis and spinal fixation system that provides superior support, as compared to a vertebral prosthesis and spinal fixation system that are not interconnected with one another. Additionally, the upper and lower outer bone screws 34 extend through the bone of inferior vertebra 50 and superior vertebra 52 to provide additional support. The unified prosthesis and fixation system may eliminate the need for spikes or other engaging mechanisms extending from the endplates that would typically be used to aid in the engagement between the prosthesis and the adjacent vertebrae because the prosthesis 10 is instead fixed in place by the bone screw 34 extending through the adjacent vertebrae 50, 52 and locking plate 32.

The system depicted in FIG. 11 is intended to address the issue of spinal fixation device bone screw migration. By anchoring the bone screws 34 used to attach the locking plate 32 into the vertebral prosthesis 10, the bone screws are intended to be less prone to migration within the vertebrae 50, 52, as compared to a spinal fixation device attached only to vertebrae. Note how the anchors 42, 44 extend into the adjacent vertebrae 50, 52 to permit the engagement of both bone and the anchors 42, 44 by the upper and lower outer bone screws 34. Further, the locking plate 32 provides an additional longitudinal support between the vertebrae 50, 52. The additional support is intended to reduce the incidence of the vertebral prosthesis collapsing into one or both of the adjacent vertebrae 50, 52 due to the vertebral prosthesis carrying all of the load between the adjacent vertebrae 50, 52.

Further referring to FIG. 11, the spacing between the apertures in locking plate 32 is intended to aid the surgeon in fastening the bone screws 34 into the prosthesis 10. The two lower apertures in the locking plate 32 may be spaced to correspond to the spacing between the two lower apertures in the prosthesis 10 so that once the lower interior bone screw 34 is inserted through the locking plate 32 and into the shaft, the lower outer bone screw 34 may be drilled into the inferior vertebra 50 and automatically guided through the aperture in anchor 44 due to the spacing between the apertures in the locking plate being configured to automatically provide the proper spacing between bone screws 34.

The slot 38 in the locking plate 32 (see FIG. 3) provides flexibility with respect to the adjustable height of vertebral prosthesis 10. When the height of the vertebral prosthesis 10 is changed during surgery, the distance between the upper and lower bone screws 34 is also changed. The slot 38 permits variability in the placement of bone screws so that a single locking plate 32 may be utilized with one adjustable height vertebral prosthesis, rather than requiring a variety of differently configured locking plates 32.

Figure 12:
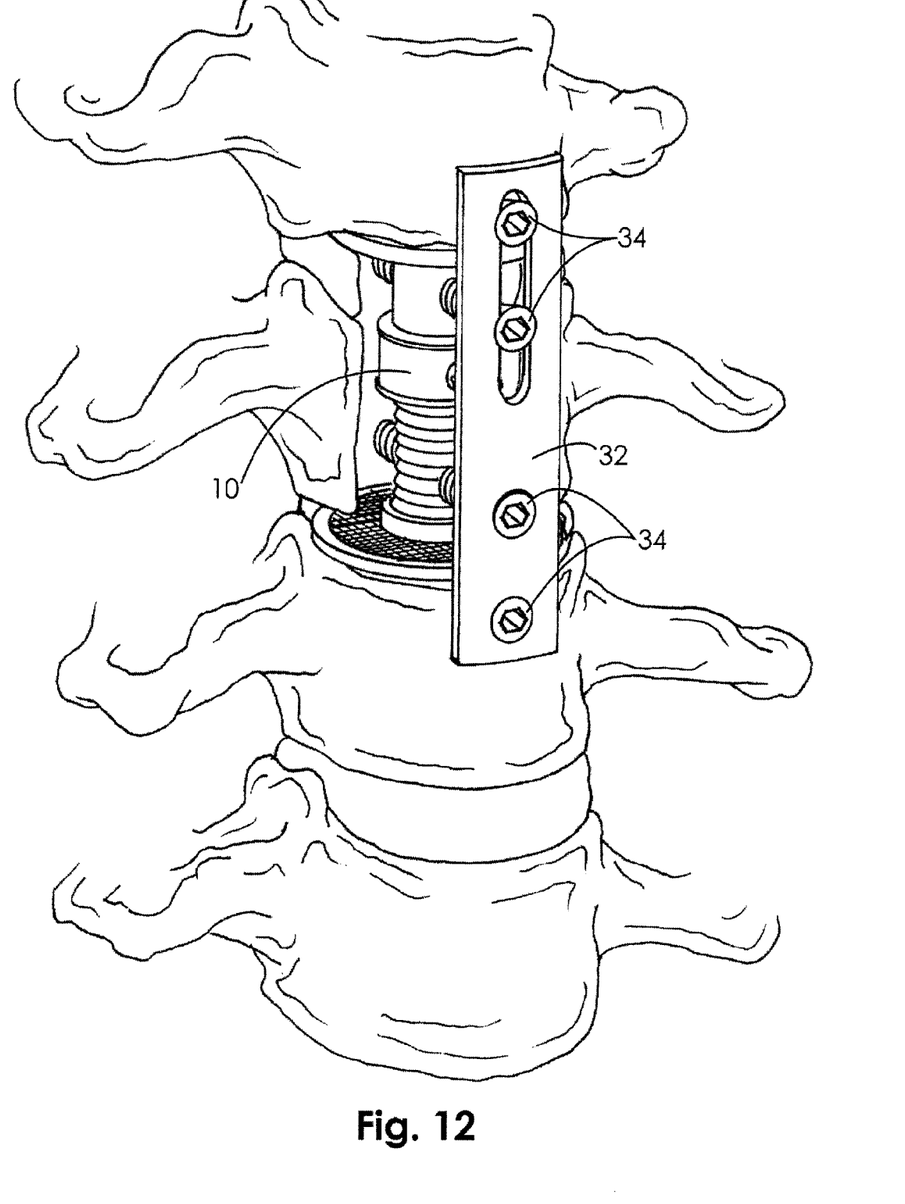
FIG. 12 is a perspective view of a vertebral prosthesis and spinal fixation plate inserted into a spine.

FIG. 11 depicts the vertebral prosthesis 10 in use with a lateral thoracolumbar locking plate. Referring to FIG. 12, the system may also be utilized with an anterior placement of the locking plate 32, such as may be utilized in the treatment of cervical burst fractures. Note that in other embodiments of the invention, additional bone screws may be utilized to attach the spinal fixation device to the vertebral prosthesis. The additional bone screws may extend through other apertures in the shaft or anchors, or may attach to additional anchoring mechanisms extending from the endplates.

The vertebral prosthesis, spinal fixation plate, and bone screws described herein may be composed of a titanium alloy, although other materials may also be suitable. The other materials may be ceramic, composite, or metallic, and may be absorbable or bioactive. Further, the vertebral prosthesis, spinal fixation plate, and bone screws may have different configurations in alternative embodiments still within the scope of the present invention.

Figure 13:
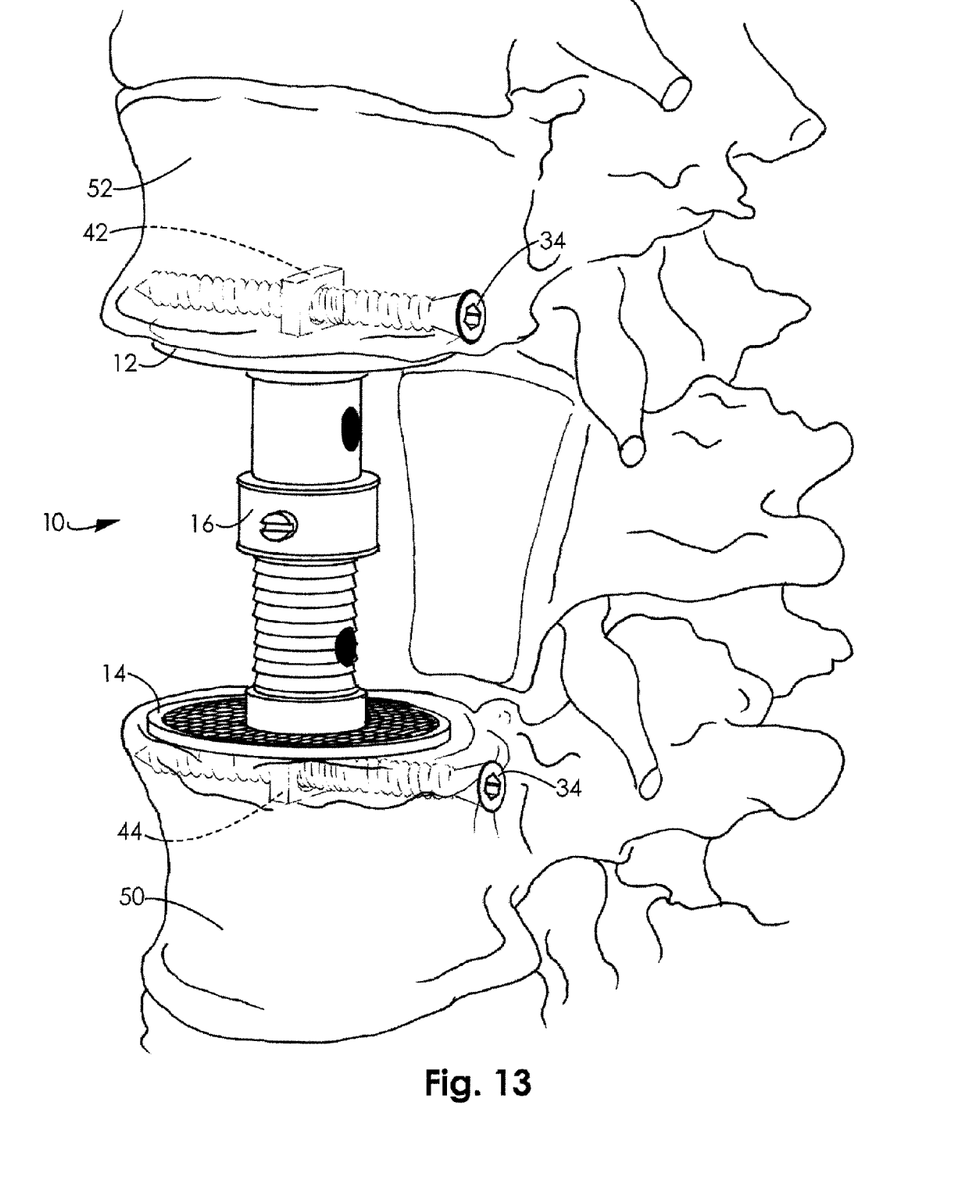
FIG. 13 is a perspective view of a vertebral prosthesis inserted into a spine.

Referring to FIG. 13, in an alternative embodiment, the vertebral prosthesis 10 may be attached to adjacent vertebrae 50, 52 with bone screws 34 without use of a locking plate. The bone screws 34 are attached to both the vertebral prosthesis and the inferior and superior vertebrae 50, 52 and therefore provide the necessary structural stability for spinal fusion to occur without the use of a supplemental spinal fixation system such as a locking plate. In other embodiments, additional bone screws may be utilized to provide the desired structural stability and may extend through additional apertures in the anchors or thorough additional anchoring mechanisms extending from the endplates.

A diseased or damaged vertebra may be replaced or reconstructed using the following exemplary procedure. As an initial matter, it must be determined that the vertebra in question must be replaced. The reasons for replacement may include a lumbar burst fracture or a cervical fracture. Prior to operating, a vertebral prosthesis will be chosen on the basis of pre-operative sizing. Depending on the location of the vertebra to be replaced or reconstructed, the surgeon will create an aperture in the patient using a lateral or anterior approach as desired. When spinal fusion is desired, the natural disks above and below the compromised vertebra will be excised along with the vertebra in question, removing the bone infringing on the nervous structures as well as most of the vertebral body.

The sizing of the vertebral prosthesis will then be confirmed intraoperatively. The inferior and superior vertebrae 50, 52 will be prepared to accept the anchors 42, 44, such as by utilizing a high speed burr to cut a channel into each of the adjacent vertebrae 50, 52 to accept the anchors 42, 44. The vertebral prosthesis may then be placed into position between the inferior and superior vertebrae 50, 52 and the bone screws 34 used to attach the locking plate 32 to the vertebral prosthesis 10, creating the combined vertebral prosthesis and spinal fixation system. Pedicle screws (not shown) may be utilized to further stabilize the vertebral prosthesis, such as by placing pedicle screws through the pedicles and into a pedicle screw attachment point on the vertebral prosthesis as shown in U.S. application Ser. No. 10/686,998.

After the vertebral prosthesis has been placed into the spine, it may be necessary to adjust the height prior to securing the prosthesis with the bone screws. The height may be adjusted in situ by loosening the screw 28 to permit the upper and lower portions 18, of the shaft 16 to be adjusted relative to one another to adjust the height of the prosthesis and retightening the screw 28 to lock the shaft at the desired height.

After insertion of the vertebral prosthesis and locking plate, bone graft or other supplementation may be placed around the vertebral prosthesis to aid in the fusion of the inferior and superior vertebrae. Further, bone graft or a supplement may be placed into the shaft prior to surgery to enhance bone ingrowth as desired. The endplates 12, 14 may have a lattice or mesh design in order to promote bone ingrowth for fusion purposes. Finally, the aperture in the patient is closed to complete the surgical procedure.

While the detailed drawings and specific examples given herein describe various exemplary embodiments, they serve the purpose of illustration only. It is to be understood that the invention is not limited in its application to the details of construction and the arrangements of components set forth in the preceding description or illustrated in the drawings. For example, the vertebral prosthesis is shown as having two bone screws inserted into the shaft and two bone screws inserted into the anchoring mechanisms, but other configurations are contemplated and are within the scope of the invention. Further, the anchor design may take different shapes and sizes depending on the type and configuration of bone screws used to attached the locking plate to the vertebral prosthesis. Furthermore, other substitutions, modifications, changes, and omissions may be made in the design, operating conditions, and arrangements of the exemplary embodiments without departing from the scope of the invention as expressed in the appended claims.

What is claimed is:

1. A spinal implant system suitable for a spinal fusion procedure, comprising:
   a vertebral prosthesis adapted to be placed at a site of an excised vertebra between two adjacent remaining vertebrae, the vertebral prosthesis comprising:
   a shaft having a first end and a second end, wherein the shaft is adjustable to alter a distance between the first end and the second end;
   a first end plate coupled to the first end of the shaft, the first end plate having an outer edge defining an outer perimeter of the first end plate;
   wherein the first end plate is locked to the shaft to create a rigid structure suitable to allow the two remaining vertebrae adjacent the vertebral prosthesis to fuse together with the vertebral prosthesis to form one rigid structure; and
   a first anchor extending from the first end plate such that the first anchor is positioned within the outer perimeter of the first end plate, the first anchor defining an aperture configured to receive and engage a bone screw, wherein the first anchor comprises a first face and a second face, wherein the aperture extends between the first face and the second face, and further wherein both the first face and the second face are located within the outer perimeter of the first end plate; and
   wherein the bone screw engages with the aperture in the first anchor to thereby secure the vertebral prosthesis at the site of the excised vertebra and form a rigid structure comprising the bone screw, the vertebral prosthesis, and the two adjacent vertebrae.

2. The spinal implant system of claim 1, further comprising:
   a second end plate coupled to the second end of the shaft, the second end plate having an outer edge defining an outer perimeter of the second end plate;
   a second anchor comprising a first face and a second face, the second anchor extending from the second end plate such that both the first face and the second face of the second anchor are positioned within the outer perimeter of the second end plate, the second anchor defining an aperture extending between the first face and the second face of the second anchor;
   a first bone screw configured to engage the aperture of the first anchor; and
   a second bone screw configured to engage the aperture of the second anchor.

3. The spinal implant system of claim 2, wherein the first anchor and the second anchor are coaxial with a longitudinal axis of the shaft.

4. The spinal implant system of claim 1, further comprising the bone screw and a spinal fixation device, wherein the bone screw extends through the spinal fixation device and into the aperture of the first anchor to thereby couple the vertebral prosthesis to the spinal fixation device.

5. The spinal implant system of claim 4, wherein when the spinal fixation device is coupled to the vertebral prosthesis, the spinal fixation device is spaced apart from the first anchor such that the outer perimeter of the first end plate is located between an inner surface of the spinal fixation device and the first anchor.

6. The spinal implant system of claim 4, wherein after implantation in a patient, a portion of the bone screw is positioned within one of the two adjacent remaining vertebrae and the portion of the bone screw is further located between the spinal fixation device and the first anchor.

7. A spinal implant system suitable for a spinal fusion procedure, comprising:
   a vertebral prosthesis adapted to be placed at a site of an excised vertebra between two adjacent remaining vertebrae, the vertebral prosthesis comprising:
   a shaft having a first end and a second end, wherein the shaft is adjustable to alter a distance between the first end and the second end;
   a first end plate coupled to the first end of the shaft, the first end plate having an outer edge defining an outer perimeter of the first end plate;
   wherein the first end plate is locked to the shaft to create a rigid structure suitable to allow the two remaining vertebrae adjacent the vertebral prosthesis to fuse together with the vertebral prosthesis to form one rigid structure; and
   a first anchor extending from the first end plate such that the first anchor is positioned within the outer perimeter of the first end plate, the first anchor defining an aperture configured to receive and engage a bone screw;
   wherein the bone screw engages with the aperture in the first anchor to thereby secure the vertebral prosthesis at the site of the excised vertebra and form a rigid structure comprising the bone screw, the vertebral prosthesis, and the two adjacent vertebrae; and
   wherein the shaft includes an outer surface defining an outer perimeter of the shaft, wherein the first anchor is positioned within the outer perimeter of the shaft.

8. A spinal implant system suitable for a spinal fusion procedure, comprising:
   a vertebral prosthesis adapted to be placed at a site of an excised vertebra between two adjacent remaining vertebrae, the vertebral prosthesis comprising:
   a shaft having a first end and a second end, wherein the shaft is adjustable to alter a distance between the first end and the second end;
   a first end plate coupled to the first end of the shaft, the first end plate having an outer edge defining an outer perimeter of the first end plate;
   wherein the first end plate is locked to the shaft to create a rigid structure suitable to allow the two remaining vertebrae adjacent the vertebral prosthesis to fuse together with the vertebral prosthesis to form one rigid structure; and
   a first anchor extending from the first end plate such that the first anchor is positioned within the outer perimeter of the first end plate, the first anchor defining an aperture configured to receive and engage a bone screw, wherein the aperture of the first anchor is threaded;
wherein the bone screw engages with the aperture in the first anchor to thereby secure the vertebral prosthesis at the site of the excised vertebra and form a rigid structure comprising the bone screw, the vertebral prosthesis, and the two adjacent vertebrae.

* * * * *